United States Patent [19]

Siele

[11] 3,979,379

[45] Sept. 7, 1976

[54] PROCESS FOR PRODUCING 1,3,5,7-TETRAALKANOYL-1,3,5,7-OCTAHYDROTETRAZOCINES

[75] Inventor: Victor I. Siele, Succasunna, N.J.

[73] Assignee: The United States of America as represented by the Secretary of the Army, Washington, D.C.

[22] Filed: Apr. 25, 1975

[21] Appl. No.: 571,877

[52] U.S. Cl. ................. 260/239 BC; 260/239 HM
[51] Int. Cl.$^2$ ...................................... C07D 257/02
[58] Field of Search ............... 260/239 BC, 239 HM

[56] References Cited
UNITED STATES PATENTS 2,941,994   5/1960   Silberman.................... 260/239 HM

FOREIGN PATENTS OR APPLICATIONS 590,851   1/1960   Canada...................... 260/239 HM Primary Examiner—Nicholas S. Rizzo
Assistant Examiner—D. B. Springer
Attorney, Agent, or Firm—Nathan Edelberg; A. Victor Erkkila

[57] ABSTRACT

1,3,5,7-Tetraalkanoyl-1,3,5,7-octahydrotetrazocines are produced in good yield by reacting a 1,5-dialkanoyl-1,3,5,7-tetraazabicyclo (3,3,1) nonane with an alkanoyl chloride, an alkanoic acid anhydride and an alkanoic acid alkali metal salt in the presence of an organic diluent.

8 Claims, No Drawings

PROCESS FOR PRODUCING 1,3,5,7-TETRAALKANOYL-1,3,5,7-OCTAHYDROTETRAZOCINES

BACKGROUND OF THE INVENTION 1,3,5,7-Tetraacetyl-1,3,5,7-octahydrotetrazocine (TAT) is an intermediate in a novel process for the production of the important military explosive HMX (1,3,5,7-tetranitro-1,3,5,7-octahydrotetrazocine), which is the subject of copending U.S. Pat. application, Ser. No. 445,738, filed Feb. 25, 1974, now U.S. Pat. No. 3,939,148, "Process For Preparing 1,3,5,7-Tetranitro-1,3,5,7-Tetraazacyclooctane," Victor I. Siele and Everett E. Gilbert, inventors. In the past TAT has been prepared by heating 1,5-diacetyl-1,3,5,7tetraazabicyclo (3,3,1) nonane (hereinafter referred to as DAPT) with acetic anhydride under anhydrous conditions, but the yields were always poor. Thus, G. C. Bassler, "The Chemistry of Cyclonite", Pennsylvania State University, PhD Thesis 1943, p. 179, obtained a 20% yield of TAT by heating DAPT with acetic anhydride containing a small amount of acetyl chloride at 95°C. for 90 minutes. Attempts to improve the yield TAT by conducting the reaction in boiling chloroform solvent (b.p. 61°C.) produced yields as high as 35% but the results were not reproducible.

SUMMARY AND DETAILED DESCRIPTION OF THE INVENTION

It is an object of the present invention to provide a process for the preparation of TAT in good yield from DAPT and acetyl chloride in conjunction with acetic anhydride. A further object of the present invention is to provide a novel process for preparing 1,3,5,7-tetraalkanoyl-1,3,5,7-octahydrotetrazocines. Other objects will appear obvious as the invention is further described.

In accordance with the process of the present invention 1,3,5,7-tetraalkanoyl-1,3,5,7-octahydrotetrazocines of the formula

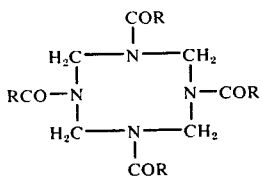

wherein R is an alkyl group of 1 to 6 carbon atoms, are prepared by reacting a 1,5-dialkanoyl-1,3,5,7-tetraazabicyclo (3,3,1) nonane of the formula

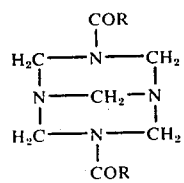

wherein R has the foregoing definition, with an alkanoic acid chloride, an alkanoic acid anhydride and an alkanoic acid salt of the following formulas, resp.

RCOCl, (RCO)₂O and RCOOMe wherein R has the foregoing definition and Me is an alkali metal, in the presence of an organic diluent.

Although the reactions involved in the process of the present invention are not precisely known, it is believed that in the presence of the sodium acetate (or equivalent) the reaction of DAPT (or equivalent) with acetyl chloride (or equivalent) and acetic anhydride (or equivalent) proceeds essentially in three steps. The first step involves opening of the endomethylene linkage and addition of acetyl chloride to form 1,3,5-triacetyl-7-chloromethyloctahydrotetrazocine (or equivalent). In the second step the chloromethyl compound reacts with sodium acetate to form the 7-acetoxymethyl derivative (or equivalent), which in the third step undergoes acylative cleavage with acetic anhydride to form TAT (or equivalent). The reactions with DAPT and equivalents are represented as follows, wherein R and Me have the aforementioned definitions.

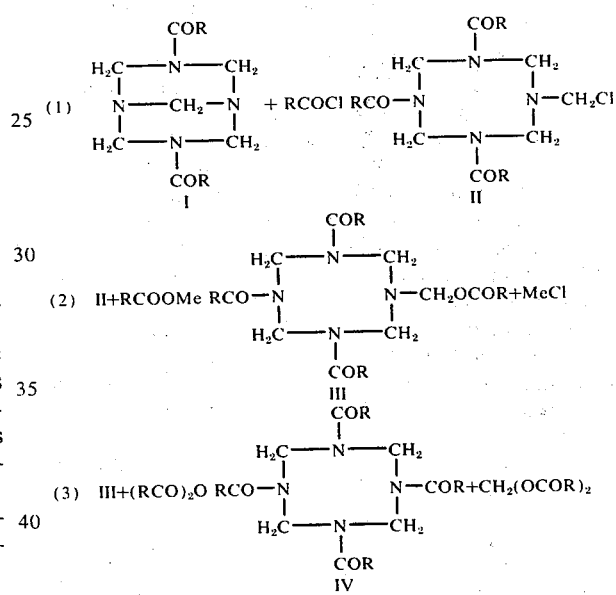

The high yields of the tetraalkanoyl compound IV, obtained by carrying out the reaction in the presence of the alkanoic acid salt according to the process of the present invention, are surprising, since in the absence of such salt little, if any, of the tetraalkanoyl compound IV is formed at room temperature, as shown in Example 12 below, and only low yields are obtained at elevated temperatures according to the aforesaid publication of G. C. Bassler. Further, the aforesaid reaction mechanism of the present process is supported by the fact that little, if any, tetraalkanoyl compound IV is formed by mixing the dialkanoyl compound I, alkanoic acid salt and either the alkanoyl chloride or the alkanoic acid anhydride, but not both, as shown in Examples 9 and 10 below.

The process of the present invention comprises reacting the dialkanoyl compound I with the alkanoyl chloride, alkanoic acid anhydride and alkali metal salt of the alkanoic acid, conveniently at ordinary temperature, and thereafter separating the tetraalkanoyl compound IV produced. Preferably, the alkanoyl chloride is added gradually to the other reactants. However, the reactants can be mixed together in any order except that the alkanoyl chloride should be added after the alkanoic acid salt has been mixed with the dialkanoyl compound I to avoid the formation of considerable side reactions and byproducts. Thus, for example, a relatively low yield of TAT was obtained when the acetyl chloride was added to DAPT before rather than after the addition of sodium acetate (see Examples 1–5 vs. 6). Further, while the present process is preferably carried out in the absence of water, it is possible to introduce water into the reaction mixture provided it is added after the dialkanoyl compound I, alkanoyl chloride and alkanoic acid salt have been mixed together and reacted (see Example 5). However, little, if any, TAT was obtained when the sodium acetate was added as a solution in water to the mixture of DAPT and acetyl chloride (cf. Examples 7 and 8). Under such conditions the water apparently reacts preferentially with the chloromethyl compound II, thus preventing the reaction thereof with the sodium acetate to form the acetoxymethyl compound III.

The liquid organic diluent is employed in sufficient amount to provide a readily stirrable reaction mixture. Preferably, the organic diluent is a solvent for the dialkanoyl starting compound I. Suitable organic solvents solvent for the dialkanoyl starting compound I. Suitable organic solvents include glacial acetic acid, acetic anhydride, hydrocarbons, e.g. toluene and ligroin, and chlorinated hydrocarbons, e.g. chloroform, methylene chloride, tetrachloroethane and chlorobenzene.

The amounts of the reactants employed in the present process can vary widely. According to the aforesaid reaction mechanism, one mole each of the alkanoyl chloride, alkanoic acid anhydride and alkanoic acid salt per mole of 1,5-dialkanoyl-1,3,5,7-tetraazabicyclo (3,3,1) nonane I are theoretically required to produce the desired tetraalkanoyl compound IV. Generally, a substantial, e.g. 50–200%, molar excess over the theoretically required amounts is used.

An advantageous feature of the present invention is that the process can be carried out fairly rapidly at room temperature (about 20°C.). The use of lower temperatures, e.g. 0°–10°C. or below is also within the scope of the present process but requires costly cooling equipment for operation at such temperatures. The process can also be conducted above room temperature, e.g. up to about 50°C., but at still higher temperatures undesirable side reactions are usually considerably accelerated, resulting in progressively lower yields of the desired tetraalkanoyl product.

As illustrated in the examples, the tetraalkanoyl compound can be isolated by distilling the organic diluent from the reaction mass, digesting the residue with water to convert unreacted alkanoic acid anhydride and chloride, adding a base, e.g. $Na_2CO_3$, to neutralize acids present, extracting the resulting mixture with a solvent for the desired tetraalkanoyl compound, e.g. chloroform, and evaporating the extract to dryness. Alternatively, when a water-miscible solvent such as glacial acetic acid is employed, the reaction mixture without evaporation of the solvent can be diluted and digested with water, neutralized and worked up in otherwise similar manner. The tetraalkanoyl compound can be purified by crystallization from a suitable solvent, such as chloroform, nitromethane, benzene and toluene.

Suitable 1,5-dialkanoyl-1,3,5,7-tetraazabicyclo (3,3,1) nonanes of the aforesaid general formula include 1,5-diacetyl-, 1,5-di-n-propionyl-, 1,5-diisobutyryl-, and 1,5-dicapronyl-1,3,5,7-tetraazabicyclo (3,3,1) nonanes. Alkanoic acid anhydrides of the foregoing general formula which can be employed in the process of the present invention include acetic anhydride, n-propionic anhydride, isobutyric anhydride, caproic anhydride and n-heptylic anhydride. Alkanoic acid chlorides of the aforesaid general formula which can be utilized in the present process are illustrated by acetyl chloride, n-propionyl chloride, n-butyryl chloride and capronyl chloride. Alkali metal salts of alkanoic acids of the foregoing general formula include the sodium, potassium and lithium salts of acetic acid, n-propionic acid, isobutyric acid, and caproic acid. Further, the dialkanoyl compound I, alkanoyl chloride, alkanoic acid anhydride and alkanoic acid salt present in the reaction mixture may contain the same or different alkyl groups R. In the former case a 1,3,5,7-tetraalkanoyl compound containing identical alkanoyl groups is obtained (However, the alkyl group R of the alkanoic acid salt can therein be different from the alkyl group R of the other reactants, since according to the aforesaid reaction mechanism the $-CH_2OCOR$ group (cf. compound III above) formed from said alkanoic acid salt is eliminated.). In the latter case a 1,3,5,7-tetraalkanoyl compound containing different alkanoyl groups, or a mixture of such compounds, is produced.

The following examples illustrate specific embodiments of the process of the present invention.

EXAMPLE 1.

200 ml. of glacial acetic acid and 58 grams (0.56 mole) of acetic anhydride were charged into a 500 ml. round-bottomed, three-necked flask fitted with a calcium chloride drying tube, and the contents were cooled to 5°–10°C. with an ice bath. 31 grams (0.38 mole) of anhydrous sodium acetate followed by 50 grams (0.094 mole) of DAPT were added and the resulting mixture was cooled to 0°–5°C. Thereafter 15 grams (0.19 mole) of acetyl chloride were added over a period of 30 minutes and the reaction mixture was agitated at 0°–5°C. for 1 hour, then diluted with 100 ml. of water and agitated at 0°–5°C. for 80 minutes. Sodium carbonate was added sufficient to produce a solid mass, which was extracted with 2000 ml. of chloroform. The extract was dried by addition of anhydrous magnesium sulfate and filtered, and the filtrate was evaporated to dryness. 20.5 grams of TAT (77% of theory) melting at 150°–7°C. were thus obtained.

EXAMPLE 2.

7.4 grams (0.094 mole) of acetyl chloride were added during about 15 minutes to an agitated mixture of 10 grams (0.047 mole) of DAPT, 29 grams (0.28 mole) of acetic anhydride, 15.5 grams (0.19 mole) of anhydrous sodium acetate and 100 ml. of glacial acetic acid at 5°–10°C. The reaction mixture thus obtained was agitated at 5°–10°C. for 1 hour, then diluted with 100 ml. of water and agitated for about 1 hour at 5°–10°C. $Na_2CO_3$ was then added to produce a solid mass, which was extracted with 1000 ml. of chloroform. The extract was dried with anhydrous $MgSO_4$, filtered and evaporated to dryness. 12 grams of TAT melting at 153°–8°C. were obtained, corresponding to 89% of theory yield.

EXAMPLE 3.

The procedure of Example 2 was repeated except that the reaction temperature was 15°–20°C. and the reaction mixture was agitated for about one hour after the addition of acetyl chloride was complete and for one hour after dilution with the water. 11.9 grams of TAT melting at 152°–7°C. were thus obtained, which corresponds to a yield of 88% of theory.

EXAMPLE 4.

The procedure of Example 2 was repeated except that the reaction temperature was 10°–15°C. and the reaction mixture was agitated for 45 minutes following the acetyl chloride addition and for 1 hour after the dilution with water. 11.5 grams of TAT melting at 150°–7°C. were obtained, corresponding to a yield of 86% of theory.

EXAMPLE 5.

7.4 grams (0.094 mole) of acetyl chloride were added during 20 minutes to an agitated mixture of 10 grams (0.047 mole) of DAPT, 15.5 grams (0.19 mole) anhydrous sodium acetate and 100 ml. of glacial acetic acid at 15°C. The mixture was then cooled to 5°C., and 70 ml. of water were quickly added, after which 29 grams (0.28 mole) of acetic anhydride were introduced over a period of 45 minutes at 5°C. The reaction mixture was agitated at 5°C. for 30 minutes and then worked up in the manner described above. 11.2 grams of TAT melting at 153°–8°C. were obtained, which corresponds to a yield of 83% of theory.

EXAMPLE 6.

7.4 grams (0.094 mole) of acetyl chloride were added during 10 minutes to a mixture of 10 grams (0.047 mole) of DAPT and 100 ml. of glacial acetic acid at 10°–15°C. 15.5 grams (0.19 mole) of anhydrous sodium acetate were then added in about 5 minutes, after which 29 grams (0.28 mole) of acetic anhydride were added over 30 minutes while maintaining the temperature at 10°–15°C. The reaction mixture was agitated at 10°–15°C. for 30 minutes, then diluted with 50 ml. of water, and mixed with sufficient sodium carbonate to produce a solid mass, which was extracted with chloroform. The extract was dried over anhydrous magnesium sulfate, filtered and evaporated to dryness. 4 grams of TAT melting at 157°–160°C. were thus obtained, which corresponds with 30% of theory yield.

EXAMPLE 7.

The procedure of Example 5 was repeated except that the sodium acetate and the water were added together as an aqueous solution to the mixture just before the acetic anhydride, and the reaction temperature was 10°C. The product was an unidentified oil.

EXAMPLE 8.

The procedure of Example 6 was repeated except that the acetic anhydride was added to the reaction mixture before the aqueous solution of the sodium acetate. The product obtained was an unidentified oil.

EXAMPLE 9.

The procedure of Example 2 was repeated except that 0.374 mole instead of 0.28 mole of acetic anhydride were added and no acetyl chloride was employed. The product obtained was essentially unreacted DAPT.

EXAMPLE 10.

The procedure of Example 2 was repeated except that 0.374 mole instead of 0.094 mole of acetyl chloride was used and no acetic anhydride was added. The product obtained was an unidentified oil, which contained a small amount of TAT (based on NMR analysis).

EXAMPLE 11.

29 grams (0.28 mole) of acetic anhydride were added during 30 minutes to an agitated mixture of 10 grams (0.047 mole) of DAPT, 15.5 grams (0.19 mole) of anhydrous sodium acetate and 100 ml. of dry chloroform at 5°–10°C. Thereafter 7.4 grams (0.094 mole) of acetyl chloride were added over a period of 15 minutes. The reaction mixture thus obtained was agitated at 5°–10°C. for 45 minutes and then filtered to remove chloroform insolubles. The filtrate was evaporated on a steambath to an oil, and the oil was dissolved in 50 ml. of water and mixed with sufficient $Na_2CO_3$ to produce a solid mass. The solid was extracted with 300 ml. of chloroform and the extract was dried with anhydrous magnesium sulfate, filtered and evaporated to dryness. 10.8 grams of TAT melting at 153°–8°C. were obtained, corresponding to 80% of theory yield.

EXAMPLE 12.

Part A.

5 grams (0.0235 mole) of DAPT and 2.4 grams (0.0235 mole) of acetic anhydride were added to 50 ml. of dry chloroform and the resulting mixture was agitated at room temperature for 12 hours. No evidence of a reaction was observed at the end of this period via NMR analysis.

Part B.

1.85 grams (0.0235 mole) of acetyl chloride were added during 10 minutes to the mixture obtained in Part A, and the resulting mixture was agitated at room temperature for 50 minutes. NMR analysis showed that no DAPT was present in the mixture at the end of this period. The mixture was then diluted with ethyl ether, producing a white, hygroscopic solid precipitate. No evidence of TAT was found via NMR analysis.

The following table summarized the results of the foregoing examples.

The foregoing disclosure is merely illustrative of the principles of this invention and is not to be interpreted in a limiting sense. I wish it to be understood that I do not desire to be limited to exact details of construction shown and described for obvious modifications will occur to a person skilled in the art.

| Ex. | Solvent (ml.) | Reactants (mole) | | | | Total Reaction Time (Minutes) | Temp. °C. | TAT | | |
|---|---|---|---|---|---|---|---|---|---|---|
| | | DAPT | NaAc | Ac₂O | AcCl | | | Grams | % Theory | m.p. °C. |
| 1 | HAc (200) | 0.094 | 0.38 | 0.56 | 0.19 | 90 | 0–5 | 20.5 | 77 | 150–7 |
| 2 | HAc (100) | 0.047 | 0.19 | 0.28 | 0.094 | 75 | 5–10 | 12 | 89 | 153–8 |
| 3 | " | " | " | " | " | 70 | 15–20 | 11.9 | 88 | 152–7 |
| 4 | " | " | " | " | " | 60 | 10–15 | 11.5 | 86 | 150–7 |
| 5 | " | " | " | " | " | 95 | 5–15 | 11.2 | 83 | 153–8 |
| 6 | " | " | " | " | " | 75 | 10–15 | 4 | 30 | 157–160 |
| 7 | " | " | " | " | " | 75 | 10 | Unidentified oil | | |
| 8 | " | " | " | " | " | 90 | 10 | Unidentified oil | | |

-continued

| Ex. | Solvent (ml.) | Reactants (mole) DAPT | NaAc | Ac₂O | AcCl | Total Reaction Time (Minutes) | Temp. °C. | TAT Grams | % Theory | m.p. °C. |
|---|---|---|---|---|---|---|---|---|---|---|
| 9 | '' | '' | '' | 0.374 | 0 | 75 | 5-10 | Unreacted DAPT | | |
| 10 | '' | '' | '' | 0 | 0.374 | 75 | 5-10 | Unidentified oil with trace of TAT | | |
| 11 | CHCl₃ (100) | '' | '' | 0.28 | 0.094 | 60 | 5-10 | 10.8 | 80 | 153-8 |
| 12A | CHCl₃ 50 | 0.0235 | 0 | 0.0235 | 0 | 720 | 20 | No reaction | | |
| 12B | '' | '' | '' | 0.0235 | 0.0235 | 60 | 20 | Unidentified hygroscopic solid No TAT found | | |

I claim:
1. In the process for producing a 1,3,5,7-tetraalkanoyl-1,3,5,7-octahydrotetrazocine of the formula

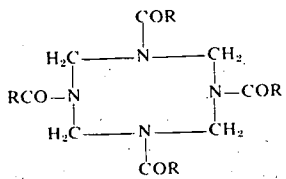

wherein R is an alkyl group of 1 to 6 carbon atoms, which comprises reacting a 1,5-dialkanoyl-1,3,5,7-tetraazabicyclo (3,3,1) nonane of the formula

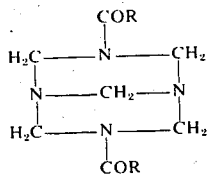

wherein R in both cases is the same and has the foregoing definition, with an alkanoyl chloride and an alkanoic acid anhydride of the formulas, resp.

RCOCl and (RCO)₂O wherein R in both cases is the same and has the foregoing definition, in the presence of an organic diluent, wherein the improvement comprises carrying out said reaction in the presence of an alkanoic acid salt of the formula RCOOMe, wherein R has the foregoing definition and Me is an alkali metal.

2. The process according to claim 1, wherein the reaction is carried out at a temperature between about 0° and 50°C.

3. The process according to claim 1, wherein the organic diluent is acetic acid.

4. The process according to claim 1, wherein the organic diluent is chloroform.

5. The process according to claim 1, wherein R is the same in each case except RCOOMe, in which R can be different.

6. The process according to claim 1, wherein the alkanoyl chloride, alkanoic acid anhydride and alkanoic acid salt are present in an amount of at least one mole per mole of the 1,5-dialkanoyl-1,3,5,7-tetraazabicyclo (3,3,1) nonane.

7. The process according to claim 1, wherein R in each case is methyl.

8. The process according to claim 7, wherein Me is sodium.

* * * * *